United States Patent [19]

Kipphan et al.

[11] Patent Number: 4,976,545
[45] Date of Patent: Dec. 11, 1990

[54] SENSOR DEVICE AND METHOD OF OPERATION

[75] Inventors: Helmut Kipphan, Schwetzingen; Josef Haase, Neckargemund, both of Fed. Rep. of Germany

[73] Assignee: Heidelberger Druckmaschinen AG, Heidelberg, Fed. Rep. of Germany

[21] Appl. No.: 252,644

[22] Filed: Sep. 30, 1988

[30] Foreign Application Priority Data

Sep. 30, 1987 [DE] Fed. Rep. of Germany ....... 3732934

[51] Int. Cl.$^5$ .................... G01B 11/30; G01N 21/84; B41F 33/10
[52] U.S. Cl. .................................. 356/446; 356/371
[58] Field of Search ................................. 356/371, 446

[56] References Cited

U.S. PATENT DOCUMENTS

| 3,922,092 | 11/1975 | Dandhker et al. | 356/371 |
| 4,677,298 | 6/1987 | Zelmanorie et al. | 356/446 |
| 4,728,196 | 3/1988 | Gerstorfer | 356/446 |
| 4,737,035 | 4/1988 | Aoki et al. | 356/446 |

FOREIGN PATENT DOCUMENTS

| 2141247 | 3/1972 | Fed. Rep. of Germany . |
| 2907620 | 8/1980 | Fed. Rep. of Germany . |
| 3037622 | 4/1982 | Fed. Rep. of Germany . |
| 3134264 | 3/1983 | Fed. Rep. of Germany . |
| 3238704 | 4/1984 | Fed. Rep. of Germany . |
| 3338611 | 7/1984 | Fed. Rep. of Germany . |
| 3304780 | 8/1984 | Fed. Rep. of Germany . |
| 3444784 | 6/1985 | Fed. Rep. of Germany . |

OTHER PUBLICATIONS

The Polygraph, pp. 140–145; "Measurement of Surface Roughness by Light Scattering Method", Techn. Nuesseu, 52nd yr, Issue 2, pp. 74–78.

M. A. Berliner, VEB Technical Publications, Berlin, "Measuring Dampness", 1st ed., 1980, pp. 108–113.

*Primary Examiner*—Richard A. Rosenberger
*Attorney, Agent, or Firm*—Herbert L. Lerner; Laurence A. Greenberg

[57] ABSTRACT

Sensor device for analyzing a surface structure includes a lighting device for emitting a focussed beam of light rays directed onto a surface, a radiation detector element for sensing light rays reflected from the surface, and an evaluating device for determining the surface structure from signals emitted by the light-ray detector element, a parameter $T_N$ for the surface structure being determinable by the evaluating device in accordance with a third moment of distribution of intensity of the reflected light rays in accordance with an equation:

$$T_N = K \sum_{i=1}^{n} (i - M)^3 P_i$$

wherein n represents a number of measuring points along a scattering indicatrix corresponding to the light rays reflected from the surface; $P_i$ is an initialized measuring signal according to an equation:

$$P_i = \frac{I_i}{\sum_{i=1}^{n} I_i}$$

wherein $I_i$ is in the intensity of the light rays on a measuring point i; K represents a scaling factor; and M has a value determinable from values for i and $P_i$ in accordance with the equation:

$$M = \sum_{i=1}^{n} i P_i.$$

12 Claims, 3 Drawing Sheets

SENSOR DEVICE AND METHOD OF OPERATION

The invention relates to a sensor device for analyzing a surface structure, including a lighting device for emitting a focussed beam of light rays directed onto a surface, a radiation detector element for sensing light rays reflected from the surface, and an evaluating device for determining the surface structure from signals emitted by the light-ray detector element; and a method of operation thereof.

A device for analyzing a surface structure has become known heretofore from German Published Non-Prosecuted Application (DE-OS) 33 04 780, wherein light reflected from a surface is measured via a light deflector array and subsequently evaluated. Illumination of the surface is effected by a beam of light generated by a light source. This conventional analyzing device is especially suited for examining or inspecting relatively smooth dry surfaces It has not been known heretofore to measure with such devices any surfaces which have been wetted with a liquid such as are used, for example, in the offset printing process.

A method is indeed known from German Published Non-Prosecuted Application (DE-OS) 34 44 784 for monitoring the ink-water ratio in lithographic printing, wherein dampening rollers are illuminated by a light source. The light reflected from the rollers is evaluated or analyzed both in the direction of the specular reflection and in the directions of diffused scattered or stray light and serves as a measure of the dampening-medium guidance.

A disadvantage of the foregoing heretoforeknown method is that the analysis or evaluation is performed only over one to four measuring points and, thereby, variations in the ink-water emulsion can be determined only with rather inadequate resolution. This means that, especially in the range of relatively small quantities of dampening medium, which are nevertheless quite relevant in printing technology, this previously known measuring method provides insufficient resolution.

Because of its limited sensitivity, therefore, this conventional method is only applicable conditionally during the actual printing run. It is barely effective during the setting-up phase A further problem with this known method is that the condition of the surfaces, which is dependent upon the material of the surfaces and other criteria, such as wear and tear, for example, exhibits a varying scattering behavior, so that the measurement of the surface remains implicitly contained in the measurement of the dampening medium, and separation is not possible.

It is accordingly an object of the invention to provide a sensor device and method of operation thereof with which the disadvantages mentioned hereinbefore are avoided and, due to which, a measurement of the surface structure of a dampened surface is able to provide a reliable statement regarding the structure and the dampened condition, respectively, as applied to the measurement of a quantity of dampening medium in offset printing technology With the foregoing and other objects in view, there is provided, in accordance with the invention, a sensor device for analyzing a surface structure comprising a lighting device for emitting a focussed beam of light rays directed onto a surface, a radiation detector element for sensing light rays reflected from the surface, and an evaluating device for determining the surface structure from signals emitted by the light-ray detector element, a parameter $T_N$ for the surface structure being determinable by the evaluating device in accordance with a third moment of distribution of intensity of the reflected light rays in accordance with an equation:

$$T_N = K \sum_{i=1}^{n} (i - M)^3 P_i$$

wherein n represents a number of measuring points along a scattering indicatrix corresponding to the light rays reflected from the surface; P is an initialized measuring signal according to an equation:

$$P_i = \frac{I_i}{\sum_{i=1}^{n} I_i}$$

wherein $I_i$ is the intensity of the light rays on a measuring point i: K represents a scaling factor and M has a value determinable from values for i and $P_i$ in accordance with the $$M = \sum_{i=1}^{n} i P_i.$$

An advantageous feature of the invention is thus that the spatial course of the intensity of the reflected radiation in accordance with a density function of a stochastic variable is characterized by moments. In particular, the slope of the distribution i.e. the third moment, serves as a measure for the condition of the surface structure, if this surface is covered with a dampening medium. It is also, in principle possible, however, to use the first and/or the second moment - the average and/or the standard deviation of the distribution—as a measure for the dampening condition of the surface.

In accordance with an alternate feature of the invention, there is provided a sensor device for determining a quantity of dampening medium deposited on a surface, comprising a lighting device for emitting a focussed beam of light rays directed onto a material surface, a radiation detector array for detecting radiation reflected from the surface, and an evaluating device for yielding from signals of the radiation detector array a characteristic factor or coefficient $T_m$ for determining the quantity of dampening medium.

Thus, a conventional device, which has heretofore been used exclusively for measuring roughness of a surface, can also be incorporated into a device for determining a quantity of dampening medium on this surface A decisive feature of the resultant device is the use of a ray detector element, so that the course of intensity of the scattering indicatrix is measured not only at a few points of the scattered radiation, but rather, at a multiplicity of the measuring points.

In accordance with another feature of the invention, there is provided a lighting device which emits radiation having wavelengths which are in the IR region. This affords the advantage that interfering light, such as daylight or outside light, for example, does not influence the measurement.

In accordance with a further feature of the invention, the parameter of the quantity of dampening medium, which was determined by the sensor device, is used as a control or regulating value in a dampening-medium control circuit. The very precise valuation of the parameter permits an especially precise automatic control of the application of the dampening medium on the printing plate.

The regulation or control during the setting-up or make-ready phase, requires nominal values to be given which, amongst other things, are dependent upon the roughness of the printing plates which are used. Thus, printing plate-dependent nominal values, determined from experience, are to be stored, and are obtained both by measuring at locations on the printing plate which are free from dampening medium and at locations thereon which conduct dampening medium. During the printing run phase, a knowledge of absolute values is not peremptorily necessary. It is enough for the purpose of controlling or regulating, to store in memory the condition which was found to be a good one, and to use the corresponding value as nominal value.

In accordance with an additional feature of the invention, the type of surface i.e. the material used, the material structure and material condition, is determinable by measuring in the dry state. This is achieved by taking a measurement of the dry surface and comparing the measured value with several stored reference values which represent a definite type or structure of surface By this comparison, the type of printing plate to be dampened can be determined and the quantity of dampening medium can be regulated to correspond to this special type.

In accordance with an added feature of the invention, the roughness of the surface is determinable by the sensor device, and a measurement for the wear of the surface is derivable therefrom. ,Thus, the wear and tear of a printing plate can be monitored continually.

In accordance with yet another feature of the invention, the characteristic factor $T_m$ is determinable in accordance with the equation:

$$T_m = K \sum_{i=1}^{n} (i - M)^m P_i$$

wherein M=an integer selected from 1 to 3, n is the number of detector elements of the radiation detector array, and $P_i$ is an initialized measurement signal according to the equation:

$$P_i = \frac{I_i}{\sum_{i=1}^{n} I_i}$$

wherein $I_i$ represents intensity of radiation on a detector element i, the value M being determinable from the values i and $P_i$ in accordance with the equation:

$$M = \sum_{i=1}^{n} i P_i$$

and K represents a scaling factor.

In accordance with yet a further feature of the invention, the radiation detector element is a row of diodes arranged so as to lie optically in a plane exposed to incident and specular reflected radiation from the lighting device.

In accordance with yet an added feature of the invention, the radiation detector element is a linearly displaceable sensor. In accordance with an alternate feature of the invention, the radiation detector element is a circularly displaceable sensor.

In accordance with yet an additional feature of the invention, the lighting device is for emitting a focussed beam of light rays having wave lengths which are in the infra-red range.

In accordance with another aspect of the invention, there is provided a method of operating the sensor device, which comprises evaluating the reflected radiation intensity of a measurement spot which is free of dampening medium so as to obtain a reference value.

In accordance with another mode, the method includes comparing the reference value with previously stored values, for determining the type of surface.

In accordance with a further mode, the method includes feeding a parameter of the quantity of dampening medium as a control value to a printing machine control circuit for feeding dampening medium.

In accordance with an additional mode, the method includes determining roughness of the surface with the sensor device, and deriving therefrom a measure for wear of the surface.

In accordance with a concomitant mode of the method of operating the sensor device, the surface structure has surface areas with varying reflection behavior in varying parts thereof, and the method includes evaluating the respective reflected radiation intensity at the varying parts of the surface areas.

Other features which are considered as characteristic for the invention are set forth in the appended claims.

Although the invention is illustrated and described herein as embodied in a sensor device, it is nevertheless not intended to be limited to the details shown, since various modifications and structural changes may be made therein without departing from the spirit of the invention and within the scope and range of equivalents of the claims The construction and method of operation of the invention, however, together with additional objects and advantages thereof will be best understood from the following description of specific embodiments when read in connection with the accompanying drawings, in which:

Before discussing the figures, it is noted that, in the offset printing process, apart from having to provide an exactly dosed input of ink, it is necessary to transfer the dampening medium, generally water with additives, in exact doses onto the printing plate, in order to achieve a predetermined ink-water balance which is required for a good printing result. Different methods have become known, heretofore, for measuring the quantity of dampening medium on the printing plate A well-known method is described, for example, in German Published Non-Prosecuted Application (DE-OS) 34 44 784 which, however, does not exhibit a degree of precision which is of the high quality required with respect to the applied quantity of dampening medium.

Figure 1:
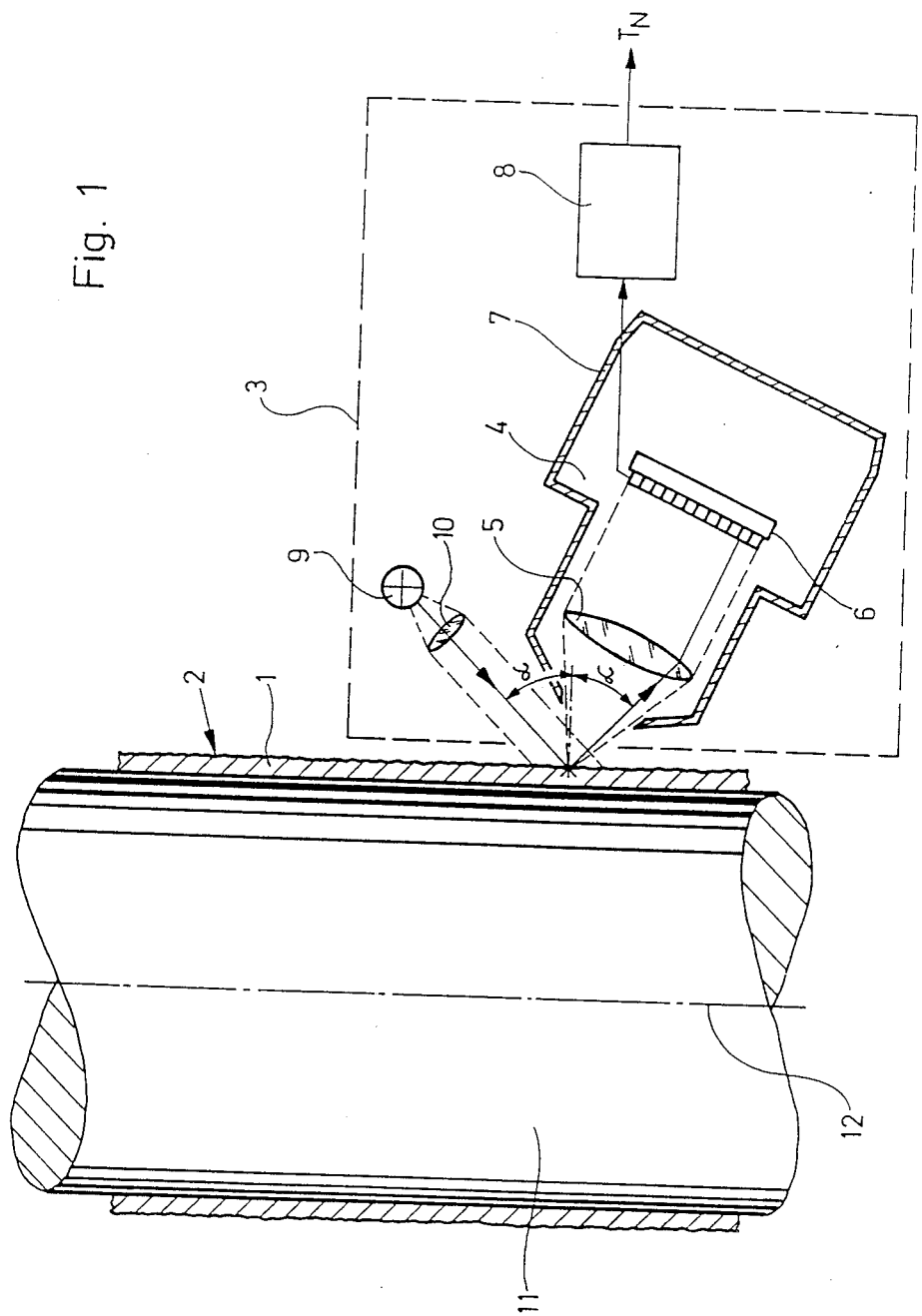
FIG. 1 is a diagrammatic view of a sensor device disposed for determining the surface structure of an object.

Referring now more particularly to the drawing, the measurement of the quantity of dampening medium is achieved in an appropriate manner, as shown in FIG. 1, on a printing plate 1 which, as is well known, has a roughened surface, and is clamped on a plate cylinder 11 of an offset printing machine. Accordingly, as shown in FIG. 1, the measurement device according to the invention is arranged in front of the rotating plate cylinder 11. The printing plate 1 is shown greatly enlarged and is only partly illustrated. A very thin film of dampening medium is disposed on the surface 2 of the printing plate 1, the quantity of dampening medium which is applied being determined with the sensor device 3. The sensor device 3 contains a measuring head 4. The measuring head 4 includes a receiving device which is known from German Published Non-Prosecuted Application (DE-OS) 33 04 780 and is made up of a receiving optical system 5, a detector array assembled as a diode row 6 and a housing 7 which encloses the entire measuring head 4. The row of diodes 6 is arranged so that it lies in an optical plane which is stepped up by the incident and reflected ray of the light source. Preferably the orientation of the measuring head is selected as shown in FIG. 1. The specular reflected ray of light falls on one of the outside diodes of the diode row 6 in the illustrated construction of the invention. It is also possible, however, to use the measurement method, if the specular reflection lies outside the row of diodes 6 or is aligned with the middle of the row.

Generally, the adjustment of the measuring head must be performed so that the reflected radiation strikes inside the row of diodes 6. This is achieved by arranging an illuminating device 9 and the measurement head 4 perpendicularly to the axis 12 of the plate cylinder 11. Further adjustment of the sensor device 3 is achieved by varying the position of the sensor device relative to the normal to the plate 1, with the result that the specular reflection is focussed on the diodes.

Figure 2:
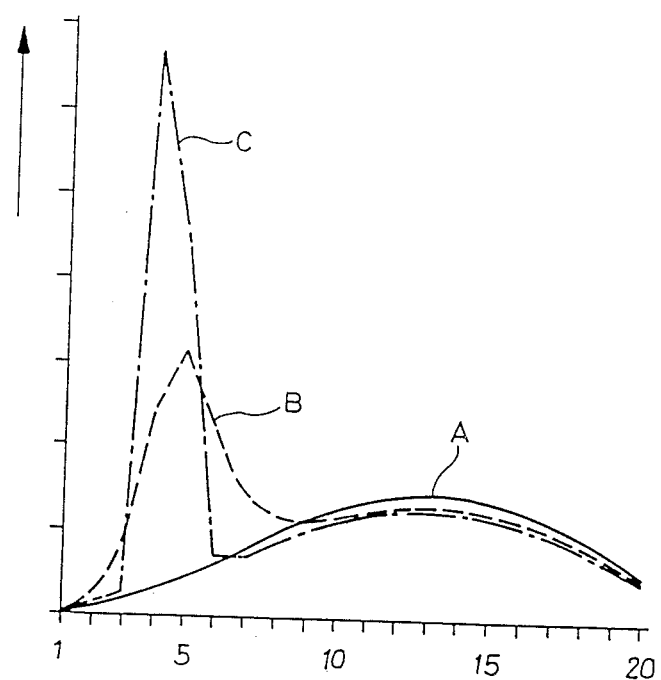
FIG. 2 is a plot diagram showing courses of scattered light for various quantities of dampening medium.
Figure 3:
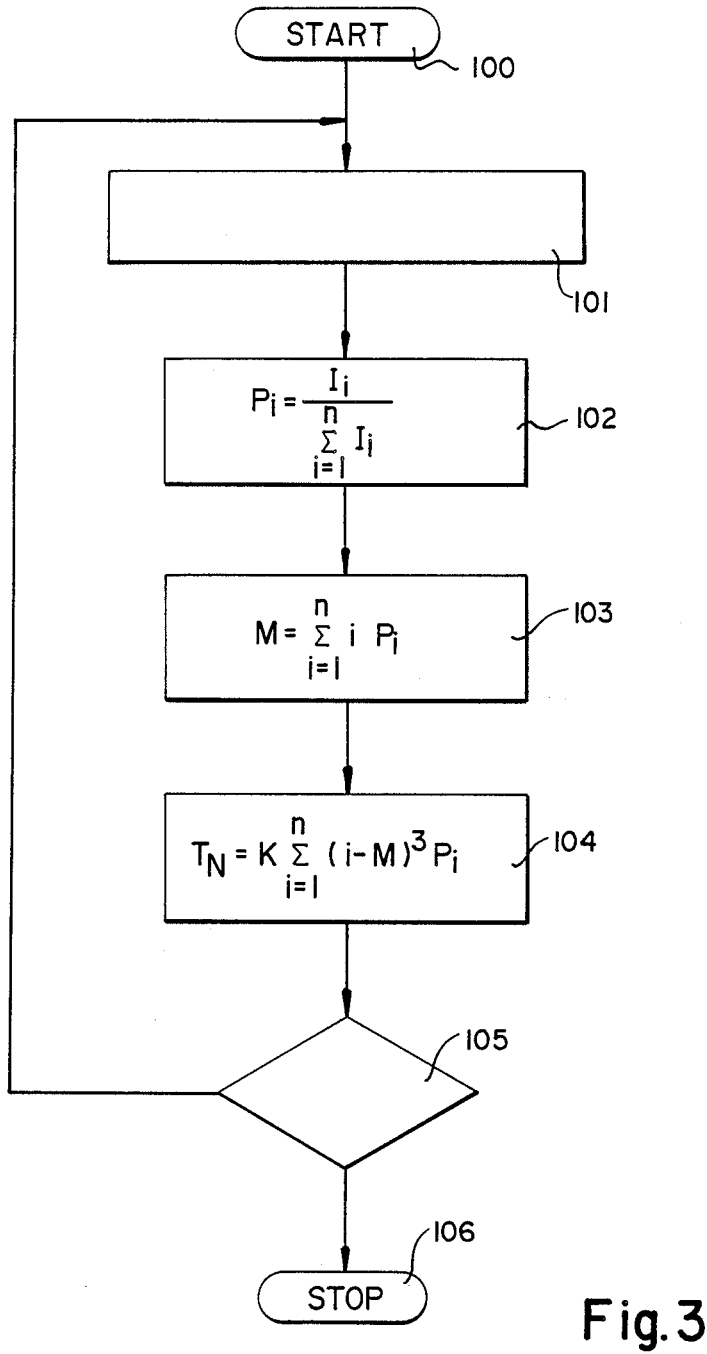
FIG. 3 is a flow diagram depicting the functions performed by the interpretation or evaluating device of FIG. 2.

The course of scattered light (scatter indicatrix) registered by the diode row 6 is fed to an interpretation or evaluating device 8, which forms or generates a parameter of the parameters $T_N$ corresponding to the quantity of dampening medium on the impression plate Scanning of the diodes of the diode row 6 by the interpretation device is effected either sequentially or in parallel, it being noted that a very high measurement and evaluation speed is achieved, in particular, by parallel scanning Illumination of the impression plate is achieved by an illuminating or lighting device 9, which casts defined light onto the printing plate via a lighting optical system 10. The arrangement of the lighting device 9 and the sensor device 3, as described hereinbefore, is such that the specular reflection lies inside the row of diodes 6. It is unnecessary for the specular reflection to strike the row of diodes 6 in the middle thereof in order to be able to evaluate or analyze the scattered light path. As is represented in FIG. 1 by the angle α, the specular reflection is located off-center or beyond the middle of the row of diodes 6. Even when one assumes that the specular reflection strikes the edge of or, in fact, even lies beyond the row of diodes 6, it is possible to obtain an analysis or evaluation of the scattered light path for the purpose of forming or generating a parameter. The lighting device 9 produces light in the infra-red region, thereby, among other things, largely eliminating disturbances by outside light In the plot diagram of FIG. 2, the intensity signal of the scattered light path via the row of diodes 6 is presented for different quantities of dampening medium. As can be seen from the values of the abscissa in FIG. 2, there are twenty diodes in the row of diodes 6. The ordinate of this diagram shows the intensity signal which is produced by the diodes. Curve A shows the intensity signal for a relatively rough printing plate which is free of dampening medium, curve B shows the intensity signal for a printing plate having relatively little dampening medium applied thereto, while curve C represents the intensity signal for a printing plate having a relatively large application of dampening medium on the surface thereof It can thus be clearly seen from the diagram of FIG. 2 that the specular reflection in the vicinity of the fourth and fifth diodes increases considerably with an increase in the quantity of dampening medium applied to the surface 2 of the printing plate 1.

It has been found to be advantageous to use moments for characterizing the spatial path of the scattered light corresponding to the density function of a stochastic variable, as a characteristic factor or coefficient for the dampening or for the quantity of dampening medium on the printing plate. In particular, the slope of the distribution i.e. the third moment, is suitable as a measure of the quantity of dampening medium on the printing plate This slope or parameter $T_N$ is defined by the equation:

$$T_N = K \sum_{i=1}^{n} (i - M)^3 P_i$$

wherein an initialized or standardized measurement signal $P_i$ is calculated in accordance with the equation:

$$P_i = \frac{I_i}{\sum_{i=1}^{n} I_i}$$

of which $I_i$ is the intensity of the radiation on a detector element i, and wherein the value M is determined from the values i and $P_i$ in accordance with the equation:

$$M = \sum_{i=1}^{n} iP_i$$

and wherein K represents a scaling factor, and n represents the number of diodes in the row of diodes. With the scaling factor K, for example, the measurement values which are relevant from a practical standpoint can be placed in a scale of from 0 to 100, in which case K would be set to the scale value 1.

For initializing or standardizing the characteristic factor $T_N$ for specific printing plates, the particular printing plate can be measured in the dry state so that starting from a dry printing plate, a corresponding reference point or reference level, respectively, can be obtained. In addition, by measuring the dry printing plate, it is possible to recognize printing or non-printing areas of the printing plate and accordingly adjust or set the position of the sensor device automatically on a non-printing area of the plate. The measurement is achieved by scanning the plate both in the direction of rotation and in the direction of the axis of the plate cylinder. Furthermore, the type of printing plate i.e. material and structure of the printing plate, can be determined automatically by measuring the dry printing plate, as a result of the varying reflection behavior of different types of printing plates, and taken into consideration in the subsequent measurement of the quantity of dampening medium. This is possible, for example, by storing in the evaluation device all reference values for various types of printing plates. If any printing plate is then measured in the dry state, the type of printing plate can be determined by comparing the measured parameter with the stored reference values, and any possibly necessary matching of the quantity of dampening medium to the special type of printing plate can be performed automatically.

The sensor device can be linked with a control circuit for controlling the quantity of dampening medium so as to be able to adjust and regulate the optimal quantity of dampening medium automatically, thereby eliminating any necessity for manual intervention in the feeding of the dampening medium during the printing process The regulation or control of the quantity of dampening medium is effected in a conventional manner by adjusting the rotational speed of the immersion or dipping roller.

It is further possible to perform with the sensor device a surface roughness measurement on the dry printing plate, in order to assess the condition of the printing plate with respect to wear and tear. Conclusions regarding the operational life and the further usefulness, respectively, of the printing plate can thus be made therefrom. Instead of the row of diodes shown in FIG. 1, a single sensor can also determine the scatter indicatrix or abscissa. It is possible, for example, to guide the sensor via a linear and/or circular movement along the scatter indicatrix and to continually determine this scatter indicatrix during the movement or within given measurement times.

Instead of a movable sensor, a deflection unit can also be arranged in front of a stationary sensor and transfer the course of the scatter indicatrix to the sensor. An evaluation or analysis of the scatter indicatrix is obtained in the aforementioned manner. With a continuous measurement-value determination and analog measurement-value processing, instead of summing the discrete measurement signals directly, the integral is formed over the course of the scatter indicatrix.

The foregoing is a description corresponding in substance to German Application P 37 32 934.0, dated September 30, 1987, the International priority of which is being claimed for the instant application, and which is hereby made part of this application. Any material discrepancies between the foregoing specification and the aforementioned corresponding German application are to be resolved in favor of the latter.

We claim:

1. Sensor device for analyzing a surface structure comprising a lighting device for emitting a focussed beam of light rays directed onto a surface, a radiation detector element for sensing light rays reflected from the surface, and an evaluating device for determining the surface structure from signals emitted by said light-ray detector element, a parameter $T_N$ for the surface structure being determinable by said evaluating device in accordance with a third moment of distribution of intensity of the reflected light rays in accordance with an equation:

$$T_N = K \sum_{i=1}^{n} (i - M)^3 P_i$$

wherein n represents a number of measuring points along a scattering indicatrix corresponding to the light rays reflected from the surface; $P_i$ is an initialized measuring signal according to an equation:

$$P_i = \frac{I_i}{\sum_{i=1}^{n} I_i}$$

wherein $I_i$ is the intensity of the light rays on a measuring point i; K represents a scaling factor; and M has a value determinable from values for i and $P_i$ in accordance with the equation:

$$M = \sum_{i=1}^{n} i P_i.$$

2. Sensor device according to claim 1, wherein said radiation detector element is a row of diodes arranged so as to lie optically in a plane exposed to incident and specular reflected radiation from said lighting device.

3. Sensor device according to claim 1, wherein said radiation detector element is a linearly displaceable sensor.

4. Sensor device according to claim 1, wherein said radiation detector element is a circularly displaceable sensor.

5. Sensor device according to claim 1, wherein said lighting device is for emitting a focussed beam of light rays having wave lengths which are in the infra-red range.

6. Method of operating the sensor device according to claim 1, wherein the surface structure has surface areas with varying reflection behavior in varying parts thereof, and which includes evaluating the respective reflected radiation intensity at the varying parts of the surface areas.

7. Sensor device according to claim 1, wherein said radiation detector element is disposed with respect to said lighting device so as to receive the reflected radiation at an off-center location.

8. Sensor device for determining a quantity of dampening medium deposited on a surface, comprising a lighting device for emitting a focussed beam of light rays directed onto a surface of an offset printing plate, a radiation detector array for detecting radiation reflected from the surface, and an evaluating device for yielding from signals of individual detector elements of said radiation detector array, in accordance with a third moment of distribution of intensity of the reflected radiation, a characteristic factor or coefficient $T_N$ for determining the quantity of dampening medium in accordance with the equation $$T_N = K \sum_{i=1}^{n} (i - M)^3 P_i$$

wherein n represents a number of measuring points along a scattering indicatrix corresponding to the light rays reflected from the surface; $P_i$ is an initialized measuring signal according to an equation:

$$P_i = \frac{I_i}{\sum_{i=1}^{n} I_i}$$

wherein $I_i$ is the intensity of the light rays on a measuring point i; K represents a scaling factor; and M has a value determinable from values for i and $P_i$ in accordance with the equation:

$$M = \sum_{i=1}^{n} iP_i.$$

9. Method of operating the sensor device according to claim 8 which comprises evaluating the reflected radiation intensity of a measurement spot which is free of dampening medium so as to obtain a reference value.

10. Method according to claim 9, which includes comparing the reference value with previously stored values, for determining the type of surface.

11. Method of operating the sensor device according to claim 8, which includes feeding a parameter of the quantity of dampening medium as a control value to a printing machine control circuit for feeding dampening medium.

12. Method of operating a sensor device for determining a quantity of dampening medium deposited on a surface, the sensor device comprising a lighting device for emitting a focussed beam of light rays directed onto a material surface, a radiation detector array for detecting radiation reflected from the surface, and an evaluating device for yielding from signals of the radiation detector array a characteristic factor $T_N$ for determining the quantity of dampening medium, and for determining roughness of the surface with the sensor device, and deriving therefrom a measure for wear of the surface.

* * * * *